(12) United States Patent
Peglion et al.

(10) Patent No.: US 8,278,440 B2
(45) Date of Patent: Oct. 2, 2012

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Pascal Caignard, Epinay-sur-Sene (FR)

(73) Assignee: Les Laboratoires Servier, Suresness Cedex (FR)

( * ) Notice: Subject to any disclaimer, the term of this patent is extended or adjusted under 35 U.S.C. 154(b) by 102 days.

(21) Appl. No.: 12/931,961

(22) Filed: Feb. 15, 2011

(65) Prior Publication Data

US 2011/0201805 A1 Aug. 18, 2011

(30) Foreign Application Priority Data

Feb. 17, 2010 (FR) ..................... 10 00657

(51) Int. Cl.
- *C07D 223/16* (2006.01)
- *C07C 47/575* (2006.01)
- *C07C 69/76* (2006.01)

(52) U.S. Cl. .................. 540/523; 560/101; 568/441
(58) Field of Classification Search ............... 540/523; 560/101; 568/441
See application file for complete search history.

(56) References Cited

FOREIGN PATENT DOCUMENTS

| WO | 2005/110993 | 11/2005 |
|---|---|---|
| WO | 2008/146308 | 12/2008 |

OTHER PUBLICATIONS

French Preliminary Search Report for FR1000657 of Jun. 28, 2010.
International Search Report for PCT/FR2011/000092 of May 30, 2011.
Laura A. McAllister, et al., Angewandte Chemie. International Edition, vol. 44, No. 3, p. 452-455, Jan. 7, 2005.

*Primary Examiner* — Bruck Kifle
(74) *Attorney, Agent, or Firm* — Hueschen and Sage

(57) ABSTRACT

Process for the synthesis of ivabradine of formula (I):

and addition salts thereof with a pharmaceutically acceptable acid.

12 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

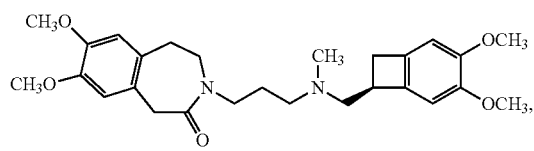
(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine hydrochloride starting from the compound of formula (II):

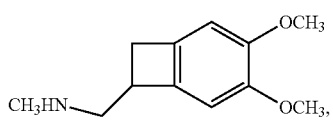
(II)

which is resolved to yield the compound of formula (III):

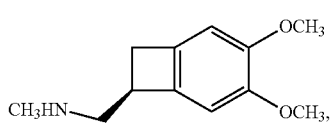
(III)

which is reacted with the compound of formula (IV):

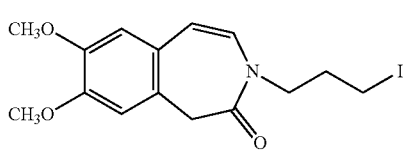
(IV)

to yield the compound of formula (V):

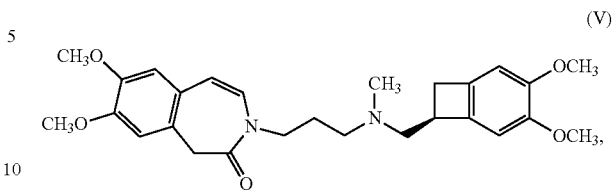
(V)

the catalytic hydrogenation of which yields ivabradine, which is then converted into its hydrochloride.

The disadvantage of that synthesis route is that it results in ivabradine in a yield of only 1%.

In view of the pharmaceutical value of this compound, it has been important to be able to obtain it by an effective synthesis process resulting in ivabradine in a good yield.

The present invention relates to a process for the synthesis of ivabradine of formula (I):

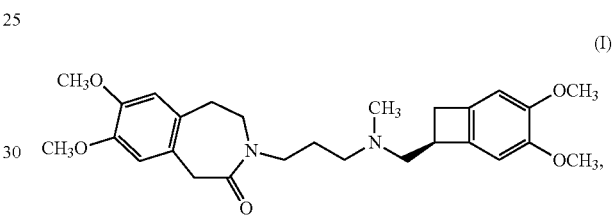
(I)

which process is characterised in that the compound of formula (VI):

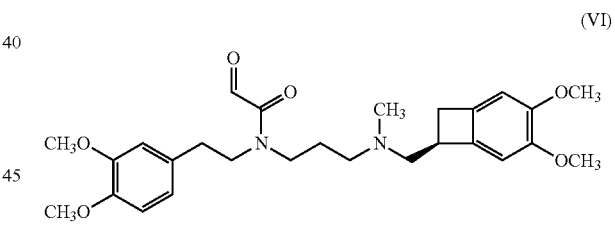
(VI)

is subjected to the action of a thiol in an organic solvent to form the hemithioacetal of formula (VII):

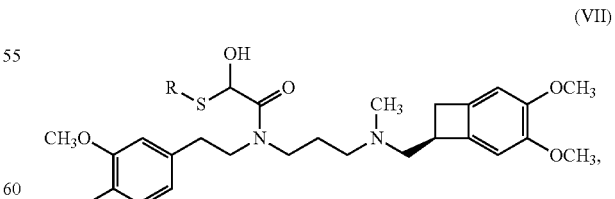
(VII)

wherein R represents a substituted or unsubstituted, optionally perfluorinated, linear or branched alkyl group, a substituted or unsubstituted aryl group, a substituted or unsubstituted benzyl group or a group $CH_2CO_2Et$, which is subjected to a cyclisation reaction to yield the compound of formula (VIII):

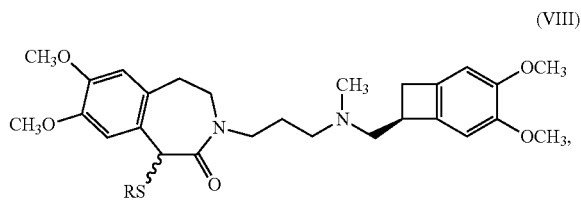

wherein R is as defined hereinbefore,
which is subjected to a reduction reaction to yield ivabradine of formula (I), which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Preference is given to the solvent used in the reaction for formation of the hemithioacetal of formula (VII) being dichloromethane.

Preference is given to the thiol selected for reacting with the compound of formula (VI) being thiophenol.

Preference is given to the solvent used for the reaction for cyclisation of the compound of formula (VII) to form the compound of formula (VIII) being dichloromethane.

In a preferred embodiment of the invention, the reaction for cyclisation of the compound of formula (VII) to form the compound of formula (VIII) is carried out in the presence of a reagent selected from acetic anhydride, trifluoroacetic anhydride and trimethylsilyl trifluoromethanesulphonate.

Greater preference is given to the reaction for cyclisation of the compound of formula (VII) to form the compound of formula (VIII) being carried out in the presence of trifluoroacetic anhydride.

Even greater preference is given to the reaction for cyclisation of the compound of formula (VII) to form the compound of formula (VIII) being carried out in the presence of trifluoroacetic anhydride and a Lewis acid selected from $BF_3.OEt_2$, $Sc(OTf)_3$ and $Yb(OTf)_3$.

Even greater preference is given to the reaction for cyclisation of the compound of formula (VII) to form the compound of formula (VIII) being carried out in the presence of trifluoroacetic anhydride and $BF_3.OEt_2$.

The reaction for reduction of the compound of formula (VIII) is preferably carried out in the presence of Raney nickel in ethanol or in the presence of samarium(II) iodide in tetrahydrofuran.

The compounds of formulae (VI), (VII) and (VIII) are new products which are useful as synthesis intermediates in the chemical or pharmaceutical industry, especially in the synthesis of ivabradine, addition salts thereof with a pharmaceutically acceptable acid and hydrates thereof, and as such they form an integral part of the present invention.

LIST OF ABBREVIATIONS USED

DMF: N,N-dimethylformamide
DMSO: dimethyl sulphoxide
THF: tetrahydrofuran
IR: infrared The Examples hereinbelow illustrate the invention.
The melting points (MP) were measured using a Kofler block (KB).
The infrared spectra were recorded on a Bruker Tensor 27 infrared apparatus with a Golden Gate ATR accessory. The substances are placed on the plate in pure form.

EXAMPLE 1 tert-butyl[2-(3,4-dimethoxyphenyl)ethyl]carbamate

Di-tert-butyl dicarbonate (12 g; 55.2 mmol) is added to a solution of 2-(3,4-dimethoxy-phenyl)ethylamine (10 g; 55.2 mmol) in dichloromethane (200 mL). After being in contact for 1 hour at ambient temperature, the reaction mixture is concentrated under reduced pressure. The residue is taken up in pentane (100 mL) and, after being in contact for 1 hour at ambient temperature, the suspension is filtered over a frit. 13.2 g of the title product are obtained in the form of a solid.
Yield=85%
m.p.=65±2° C.

EXAMPLE 2 tert-butyl 3-[{[(7S)-3,4-dimethoxybicyclo[4.2.0] octa-1,3,5-trien-7-yl]-methyl}(methyl)amino]propyl-[2-(3,4-dimethoxyphenyl)ethyl]carbamate NaH (60% in oil) (1.14 g; 28.5 mmol) is added, in small fractions, at ambient temperature, to a solution of the compound obtained in the step above (7.6 g; 27 mmol) in 40 mL of DMF. After being in contact for 1 hour at ambient temperature, a solution of 3-chloro-N-{[(7S)-3,4-dimethoxybicyclo[4.2.0]octa-1,3,5-trien-7-yl]methyl}-N-methyl-1-propanamine (7.68 g; 27 mmol) in 16 mL of DMF is added and then the reaction mixture is heated at 80° C. for 3 hours. After cooling to ambient temperature, the reaction mixture is poured into a mixture of distilled water and ice. The aqueous phase is extracted with ethyl acetate. The combined organic phases are dried over $MgSO_4$ and then concentrated under reduced pressure. The residue is purified by chromatography on silica ($CH_2Cl_2$/EtOH: 95/5) and 9.1 g of the title product are obtained in the form of an oil.
Yield=64%
IR: ν=3340, 1678, 1519, 1167 $cm^{-1}$.

EXAMPLE 3

N-{[(7S)-3,4-dimethoxybicyclo[4.2.0]octa-1,3,5-trien-7-yl]methyl}-N'-[2-(3,4-dimethoxyphenyl)ethyl]-N-methyl-1,3-propanediamine 9 g (17 mmol) of the compound obtained in the step above are dissolved in a 2.8N ethanolic HCl solution. After being in contact for 2 hours at ambient temperature, the reaction mixture is concentrated under reduced pressure. The residue is taken up in 1N sodium hydroxide solution and then the aqueous phase is extracted with ethyl acetate. After drying of the organic phase over $MgSO_4$ and then concentration under reduced pressure, 6.8 g of the title product are obtained in the form of an oil.

Yield=93%

IR: ν=3304, 2793, 1261, 1236, 1205, 1153 cm$^{-1}$.

EXAMPLE 4

N-{3-[{[(7S)-3,4-dimethoxybicyclo[4.2.0]octa-1,3,5-trien-7-yl]methyl}-(methyl)amino]propyl}-N-[2-(3,4-dimethoxyphenyl)ethyl]-2-hydroxyacetamide

Step 1: 2-{{3-[{[(7S)-3,4-dimethoxybicyclo[4.2.0]octa-1,3,5-trien-7-yl]methyl}(methyl)-amino]propyl}-[2-(3,4-dimethoxyphenyl)ethyl]amino}-2-oxo-ethyl acetate To a solution of the compound obtained in the step above (6.8 g; 15.8 mmol) in 200 mL of dichloromethane there are added, at 0° C., triethylamine (3.1 g; 22 mmol) and then, dropwise, acetoxyacetyl chloride (2.1 mL; 19 mmol). After being in contact for 0.5 hour at ambient temperature, the reaction mixture is washed with distilled water and then the organic phase is dried over $MgSO_4$. After concentrating the organic phase under reduced pressure, 8 g of the title product are obtained in the form of an oil and used in the next step without purification.

Step 2: N-{3-[{[(7S)-3,4-dimethoxybicyclo[4.2.0]octa-1,3,5-trien-7-yl]methyl}(methyl)-amino]propyl}-N-[2-(3,4-dimethoxyphenyl)ethyl]-2-hydroxy-acetamide $K_2CO_3$ (8.3 g; 60.4 mmol) is added to a solution of the compound obtained in the step above (8 g) in 80 mL of a water/methanol mixture (2/1). After being in contact for 1 hour at ambient temperature, the reaction mixture is concentrated under reduced pressure and then the residue is taken up in distilled water. After extraction with ethyl acetate, the combined organic phases are dried over $MgSO_4$ and then concentrated under reduced pressure. 6.2 g of the title product are obtained in the form of an oil.

Yield=81% (2 steps)

IR: ν=3406, 2794, 1641, 1261, 1236, 1205, 1153 cm$^{-1}$.

EXAMPLE 5

N-{3-[{[(7S)-3,4-dimethoxybicyclo[4.2.0]octa-1,3,5-trien-7-yl]methyl}-(methyl)amino]propyl}-N-[2-(3,4-dimethoxyphenyl)ethyl]-2-oxoacetamide To a solution of oxalyl chloride (0.6 mL; 6.77 mmol) in 25 mL of dichloromethane there is added, at −78° C., a solution of DMSO (0.9 mL; 12.32 mmol) in 5 mL of dichloromethane. After being in contact for 1 hour at −78° C., a solution of the compound obtained in the step above (3 g; 6.16 mmol) in 25 mL of dichloromethane is added over 0.5 hour. After being in contact for 1 hour at −78° C., triethylamine (4.3 mL; 30.8 mmol) is added; then the reaction mixture is stirred for 3 hours at ambient temperature and then poured into saturated aqueous $NaHCO_3$ solution. The organic phase is dried over $MgSO_4$ and then concentrated under reduced pressure. 2.7 g of the title product are obtained in the form of an oil.

Yield=89%

IR: ν=2788, 1645, 1589, 1261, 1236, 1207, 1151 cm$^{-1}$.

EXAMPLE 6

3-{3-[{[(7S)-3,4-dimethoxybicyclo[4.2.0]octa-1,3,5-trien-7-yl]methyl}-(methyl)amino]propyl}-7,8-dimethoxy-1-(phenylsulphanyl)-1,3,4,5-tetrahydro-2H-3-benzazepin-2-one Thiophenol (0.53 mL; 5.17 mmol) is added to a solution of the compound obtained in the step above (2.6 g; 5.17 mmol) in 60 mL of dichloromethane. After being in contact overnight at ambient temperature, there are added, in succession, trifluoroacetic anhydride (6.5 mL; 47 mmol) and then $BF_3.OEt_2$ (6.5 mL; 26 mmol). The reaction mixture is stirred for 3 hours at ambient temperature and then poured into saturated aqueous $NaHCO_3$ solution. The residue obtained after drying the organic phase over $MgSO_4$ and then concentrating under reduced pressure is purified by chromatography on silica ($CH_2Cl_2$/EtOH/$NH_4OH$ 28%:97/3/0.3). 1.15 g of the title product are obtained in the form of an oil.

Yield=38%

IR: ν=2790, 1641, 1245, 1205, 1174 cm$^{-1}$.

EXAMPLE 7

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one Raney nickel (2.5 g) (50% in $H_2O$) is added to a solution of the compound obtained in the step above (0.8 g; 1.39 mmol) in ethanol. After being in contact for 1 hour at reflux, the suspension is cooled and then filtered over Celite. 600 mg of the title product are obtained in the form of an oil.

Yield=94%

IR: ν=2788, 1646, 1519, 1461, 1245, 1105 cm$^{-1}$.

EXAMPLE 8

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one hydrochloride The title product is prepared, starting from the product obtained in the step above, by following the procedure described in patent specification EP 0 534 859 (Example 2, Step E).

The invention claimed is:

1. A process for the synthesis of ivabradine of formula (I):

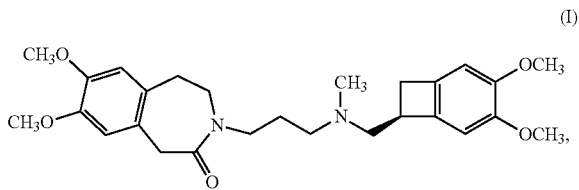

wherein a compound of formula (VI):

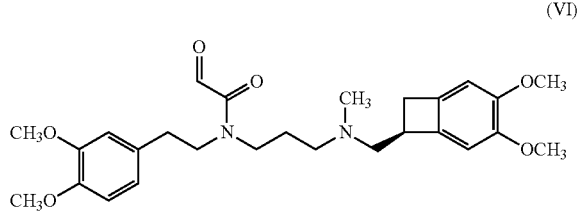
(VI)

is subjected to the action of a thiol in an organic solvent to form a hemithioacetal of formula (VII):

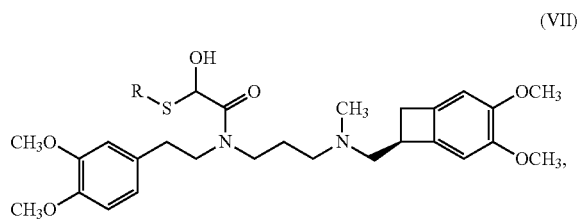
(VII)

wherein R represents a substituted or unsubstituted, optionally perfluorinated, linear or branched alkyl group, a substituted or unsubstituted aryl group, a substituted or unsubstituted benzyl group or a CH$_2$CO$_2$Et group, which is subjected to a cyclisation reaction to yield a compound of formula (VIII):

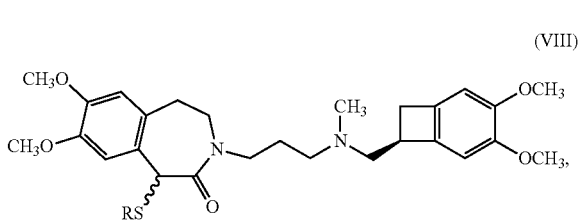
(VIII)

wherein R is as defined hereinbefore, which is subjected to a reduction reaction to yield ivabradine of formula (I), which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

2. The process of claim 1, wherein the organic solvent used in the reaction for formation of the hemithioacetal of formula (VII) is dichloromethane.

3. The process of claim 1, wherein the thiol that is reacted with the compound of formula (VI) is thiophenol.

4. The process of claim 1, wherein the solvent used in the reaction for cyclisation of the compound of formula (VII) to form the compound of formula (VIII) is dichloromethane.

5. The process of claim 1, wherein the reaction for cyclisation of the compound of formula (VII) to form the compound of formula (VIII) is carried out in the presence of a reagent selected from acetic anhydride, trifluoroacetic anhydride and trimethylsilyl trifluoromethanesulphonate.

6. The process of claim 5, wherein the reaction for cyclisation of the compound of formula (VII) to form the compound of formula (VIII) is carried out in the presence of trifluoroacetic anhydride.

7. The process of claim 6, wherein the reaction for cyclisation of the compound of formula (VII) to form the compound of formula (VIII) is carried out in the presence of trifluoroacetic anhydride and a Lewis acid selected from BF$_3$.OEt$_2$, Sc(OTf)$_3$ and Yb(OTf)$_3$.

8. The process of claim 7, wherein the reaction for cyclisation of the compound of formula (VII) to form the compound of formula (VIII) is carried out in the presence of trifluoroacetic anhydride and BF$_3$.OEt$_2$.

9. The process of claim 1, wherein the reaction for reduction of the compound of formula (VIII) is carried out in the presence of Raney nickel in ethanol or in the presence of samarium(II) iodide in tetrahydrofuran.

10. A compound of formula (VI):

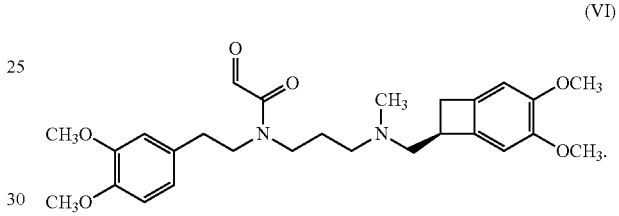
(VI)

11. A compound of formula (VII):

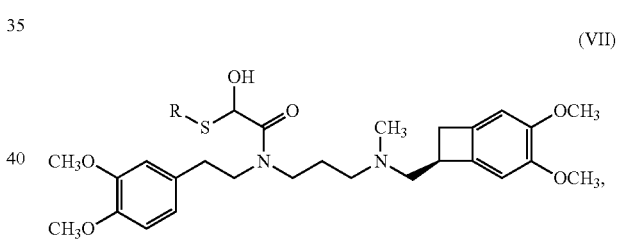
(VII)

wherein R represents a substituted or unsubstituted, optionally perfluorinated, linear or branched alkyl group, a substituted or unsubstituted aryl group, a substituted or unsubstituted benzyl group or a CH$_2$CO$_2$Et group.

12. A compound of formula (VIII):

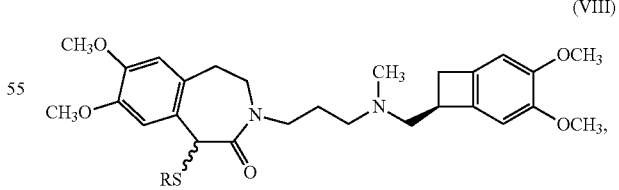
(VIII)

wherein R represents a substituted or unsubstituted, optionally perfluorinated, linear or branched alkyl group, a substituted or unsubstituted aryl group, a substituted or unsubstituted benzyl group or a CH$_2$CO$_2$Et group.

* * * * *